(12) United States Patent
Melvås

(10) Patent No.: US 6,938,474 B2
(45) Date of Patent: Sep. 6, 2005

(54) SENSING DEVICE AND METHOD FOR MEASURING FEATURES IN A FLUID

(75) Inventor: Patrik Melvås, S-126 52 Hägersten, Vapengatan 20 (SE)

(73) Assignee: Patrik Melvas, Taby (SE)

( * ) Notice: Subject to any disclaimer, the term of this patent is extended or adjusted under 35 U.S.C. 154(b) by 0 days.

(21) Appl. No.: 10/240,089

(22) PCT Filed: Mar. 22, 2001

(86) PCT No.: PCT/SE01/00619
§ 371 (c)(1),
(2), (4) Date: May 13, 2003

(87) PCT Pub. No.: WO01/75409
PCT Pub. Date: Oct. 11, 2001

(65) Prior Publication Data
US 2003/0176850 A1 Sep. 18, 2003

(30) Foreign Application Priority Data
Apr. 4, 2000 (SE) .......................................... 0001213-8

(51) Int. Cl.[7] ............................................... G01F 1/68
(52) U.S. Cl. .................................... 73/204.26; 600/505
(58) Field of Search ......................... 73/204.26, 204.25, 73/204.22, 204.11, 202.5; 600/481, 483, 485, 486, 488, 504, 505

(56) References Cited

U.S. PATENT DOCUMENTS

| | | |
|---|---|---|
| 3,587,076 A | 6/1971 | Grover |
| 4,107,987 A | 8/1978 | Robbins et al. |
| 4,142,148 A | 2/1979 | Johansson |
| 4,477,230 A | 10/1984 | Knox et al. |
| 5,588,438 A * | 12/1996 | McKown et al. ........... 600/505 |
| 5,715,827 A | 2/1997 | Corl et al. |
| 6,089,103 A * | 7/2000 | Smith ...................... 73/861.05 |

FOREIGN PATENT DOCUMENTS

| | | |
|---|---|---|
| GB | 2266956 A | 11/1993 |
| WO | WO 9727802 A1 | 8/1997 |
| WO | WO 9828725 A2 | 7/1998 |

* cited by examiner

Primary Examiner—Edward Lefkowitz
Assistant Examiner—Corey D. Mack (57) ABSTRACT

A method and a device for measuring features in a fluid such as pressure, flow rate, and temperature measurements is disclosed. The sensing device includes at least two sensing elements, all of which are mounted and/or fabricated on a chip and connected to a chip circuit, and a power supply and measuring circuit placed outside the chip and connected to the chip circuit. According to the invention the power supply and measuring circuit is controllable to feed at least two different kinds of signaling to the chip circuit. Furthermore the sensing elements are connected to each other and to the power supply and measuring circuit such that at least one of the sensing elements, controllable by the signaling from the power supply, can be individually measured. The chip is adapted to be mounted on a catheter or a guide wire.

18 Claims, 12 Drawing Sheets

SENSING DEVICE AND METHOD FOR MEASURING FEATURES IN A FLUID

CROSS REFERENCE TO RELATED APPLICATIONS

This case is a 371 of PCT/SE01/00619 filed on Mar. 22, 2001.

FIELD OF THE INVENTION

The present invention relates to a sensing device for feature measurements, for example pressure and/or flow rate and temperature measurements, in a fluid, comprising at least two sensing elements all mounted and/or fabricated on a chip and connected to a chip circuit, and a power supply and measuring circuit placed outside the chip and connected to the chip circuit.

It also relates to a method for measuring at least two different features, for example pressure and/or flow rate and temperature, the measuring being provided by at least two sensing elements all mounted and/or fabricated on a chip and connected to a chip circuit, the chip circuit being connected to a power supply and a measuring circuit placed outside the chip.

BACKGROUND OF THE INVENTION

Figure 1A:
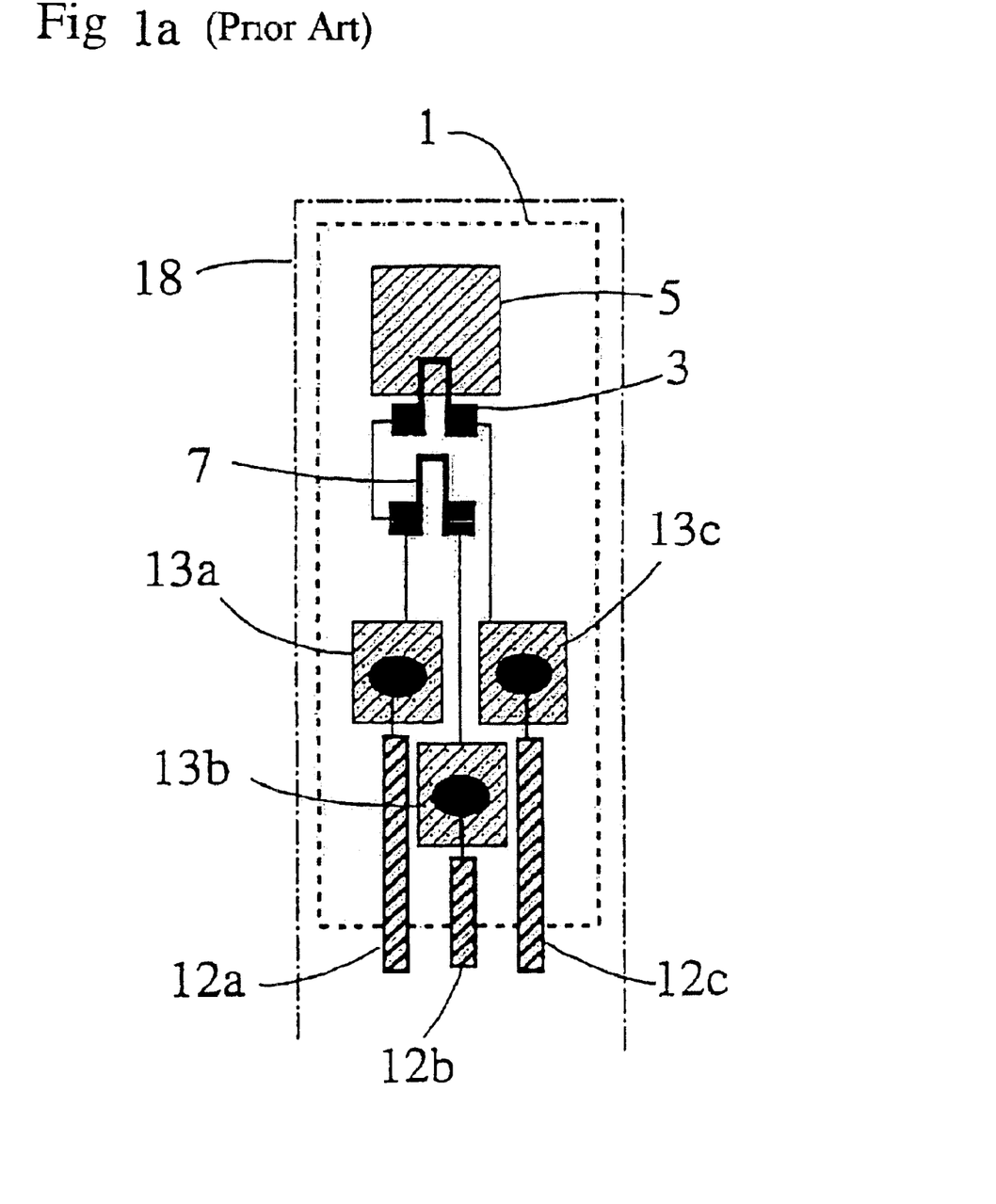
FIG. 1a shows a schematic view of a prior art pressure sensing chip adapted to be placed at the distal end of a catheter for measuring blood pressure.

Such sensing devices, mounted on a chip at the end of a catheter, are commonly used for measuring blood pressure. One example is described in WO 9727802. Such a prior art chip 1 mounted at the end of a catheter/guide wire (from here on referred to as a catheter) 18 is schematically shown in FIG. 1a. A pressure sensing element 3 is in this example a piezoresistor 3 mounted on a pressure sensitive diaphragm 5. There could also be more than one piezoresistor mounted on the diaphragm for measuring the pressure. Since piezoresistors are very sensible for temperature variations it is common to place a temperature sensing element 7 close to the pressure sensing element 3. This temperature sensing element 7 is often also a piezoresistor 7 of the same type as the pressure sensing element 3, but it is placed essentially unaffected by pressure, i.e. not on a pressure sensing element. The measuring values obtained from the temperature sensing element 7 are used for compensating the pressure measurements for the temperature effect.

Figure 1B:
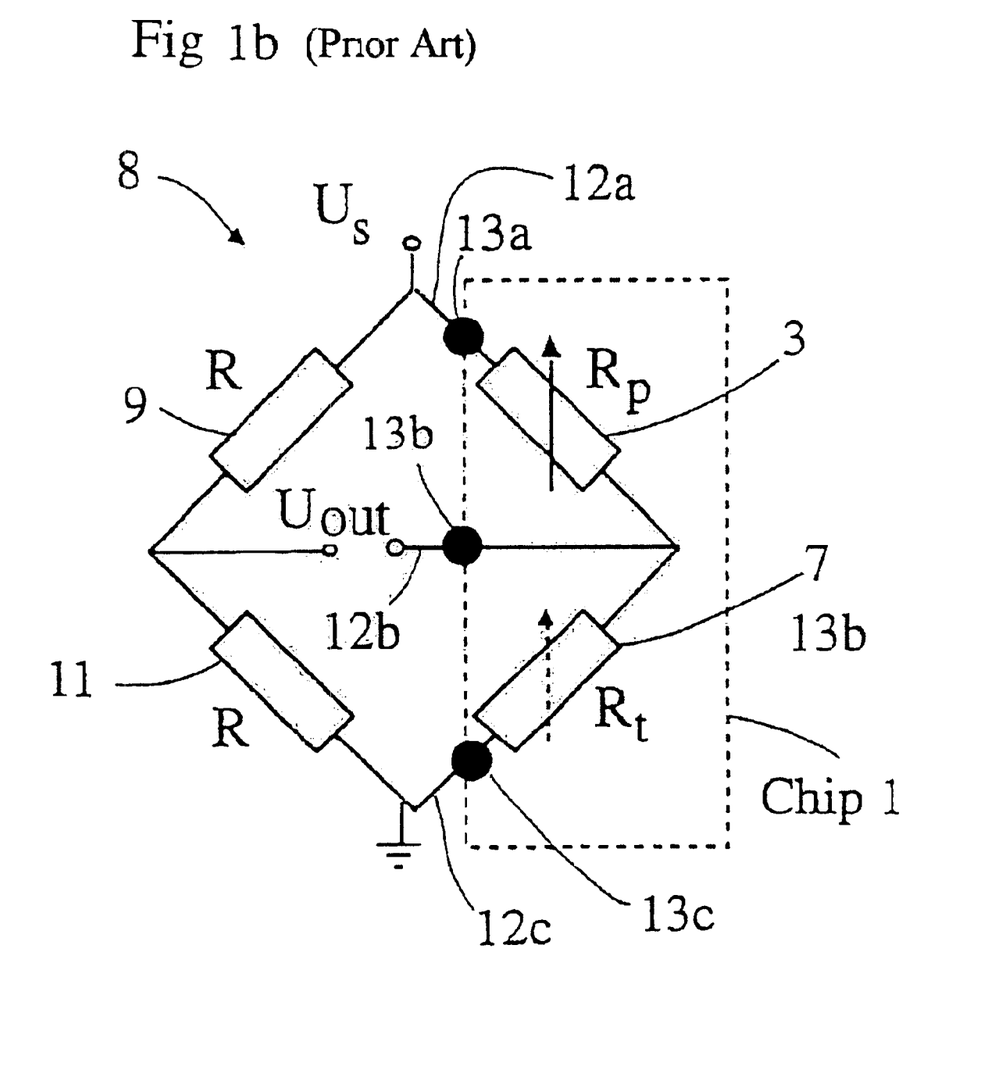
FIG. 1b shows a wiring diagram of the prior art pressure sensing chip where the pressure sensing element and the temperature sensing element are included.

A wiring diagram common for these measurements is shown in FIG. 1b. The diagram comprises both the components on the chip 1 in FIG. 1a and means R, Us, Uout placed somewhere at the other end of the catheter 18, located outside the body during measurements. As apparent in FIG. 1b, it is common to connect the temperature sensing element, Rt, 7 and the pressure sensing element, Rp, 3 to one branch each in a Wheatstone bridge 8 where two further resistors 9,11 are located each in one bridge branch at the other end of the catheter 18, i.e. outside the body during measurements. This implies that three conductors 12a,12b, 12c have to be connected to the chip 1 (shown in FIG. 1a). The conductors 12a,12b,12c are soldered onto one terminal pad 13a,13b,13c each. The pads are in turn connected to the piezoresistors 3, 7. The conductors 12a,12b,12c are isolated from each other and enclosed in the catheter 18 leading from the chip 1 to outside the body.

Another way of reducing the temperature offset in a pressure sensor is described in U.S. Pat. No. 5,715,827. The method used here is to provide two pressure sensitive piezoresistors on the chip and connected to a circuit outside the chip so as to form a Wheatstone bridge with one piezoresistor in each one of two of the bridge branches. This coupling corresponds to the one shown in FIG. 1b and thus three conductors are needed out from the chip. The two piezoresistors are both sensitive for pressure but they change their resistances with opposite signs due to pressure changes. Because of the coupling in a Wheatstone bridge the resistance changes due to pressure changes are additive and the resistance changes due to temperature changes are subtractive. This implies that if the piezoresistors are perfectly matched the temperature dependence will cancel out.

The soldering of the wires to the pads is an expensive process. Actually the mounting cost of the chip is many times bigger than the material cost in the chip. Also it is a problem that the three wires have to be isolated from each other in the catheter and that the catheter needs to be very thin.

SUMMARY

The object of the present invention is to provide a feature sensing device, for example for measuring pressure, flow rate and temperature inside the body, that is easier and cheaper to produce than the prior art pressure sensors.

Another object of the invention is to provide a sensing device, for example for measuring pressure, flow rate and temperature inside the body, connectable to a catheter being more flexible and/or thinner than what is common today.

A further object of the present invention is to provide a sensing device mounted on a catheter that measures two or more phenomena, for example pressure and temperature, using at the most two conductors out from the sensing device.

Still a further object of the invention is to provide a sensing device that can be miniaturized in such extent that it can be inserted by a catheter for in vivo measurements.

These objects have been achieved by a sensing device of the initially defined kind, which is characterised in that the power supply and measuring circuit is controllable to feed at least two different kinds of signaling to the chip circuit; and in that the at least two sensing elements are connected to each other and to the power supply and measuring circuit such that at least one of the sensing elements in dependence of the different signaling from the power supply could be individually measured and in that the chip is adapted to be mounted on a catheter or a guide wire.

They have also been achieved by a method of the initially defined kind, which is characterised by mounting the chip on a catheter or a guide wire and inserting the catheter or guide wire into the actual measuring place and controlling the power supply and measuring circuit to feed at least two different kinds of signals to the chip circuit, measuring at least two different features and deriving a value in a processing means connected to a measuring output of the measuring circuit by comparing the at least two different measurements, the derived value being the temperature compensated value for at least one of the features.

Hereby a sensing device that measures at least two different features and just needs two conductors at the most out from the chip is achieved.

Preferably at least one of the sensing elements is a temperature sensing element provided to compensate for the temperature dependence in the other sensing elements.

Suitably all the sensing elements are connected in parallel with one another or each of the other sensing elements is connected in parallel with one individual of the at least one temperature sensing element.

Preferably at least one of the parallel coupled elements is connected in series with control means permitting current to pass only when it is controlled in such sense from the power supply and measuring circuit. This makes it possible, by control from the power supply, to measure only one of the sensing elements at time.

Suitably the power supply is controlled by changing the direction and/or the output level of a DC supply and/or by changing the frequency and/or amplitude of an AC supply.

The at least one control means permits preferably only rectified current in one direction to pass and the control of the power supply is then provided by polarising its supply voltage or current in opposite directions.

The catheter or guide wire is suitably inserted into a body for in vivo measurements.

Preferably the connected sensing elements on the chip together form one branch of a Wheatstone bridge where the power supply and the measuring circuit outside the chip comprises the other branches of the bridge. This simplifies the measuring procedure.

The sensing device comprises suitably processing means, PC, connected to a measuring output of the measuring circuit, the processing means being adapted to store the output after each control from the power supply and by comparing the stored values with calibration values for the sensing elements concerned provide as an output value the temperature compensated sensed feature.

Suitably the sensing device is adapted to measure at least two different phenomena and transmit at least two different measurements through at the most two conductors.

Preferably the sensing elements comprise at least one temperature sensing element and at least one temperature and pressure sensing element, the temperature sensing element being a piezoresistor and/or a diode and the temperature and pressure sensing element being a piezoresistor lying on a pressure sensitive diaphragm. This enables pressure measurements with temperature compensation.

A first conductor is suitably connected to one side of the parallel connected sensing elements and a second conductor is connected to the other side of the parallel connected sensing elements, whereby the conductors either both are enclosed in a catheter leading from the chip or one of the conductors is the catheter itself and/or one of the conductors is a conductive liquid or gas or a combination of them in where the feature is measured.

In one embodiment of the invention the sensing device is adapted to be coupled in series or in parallel to at least one other sensing device such that different measurement values can be derived from the two sensing devices by changing the polarity/phase and/or the amplitude of the voltage/current supply.

DETAILED DESCRIPTION OF EMBODIMENTS

Figure 2A:
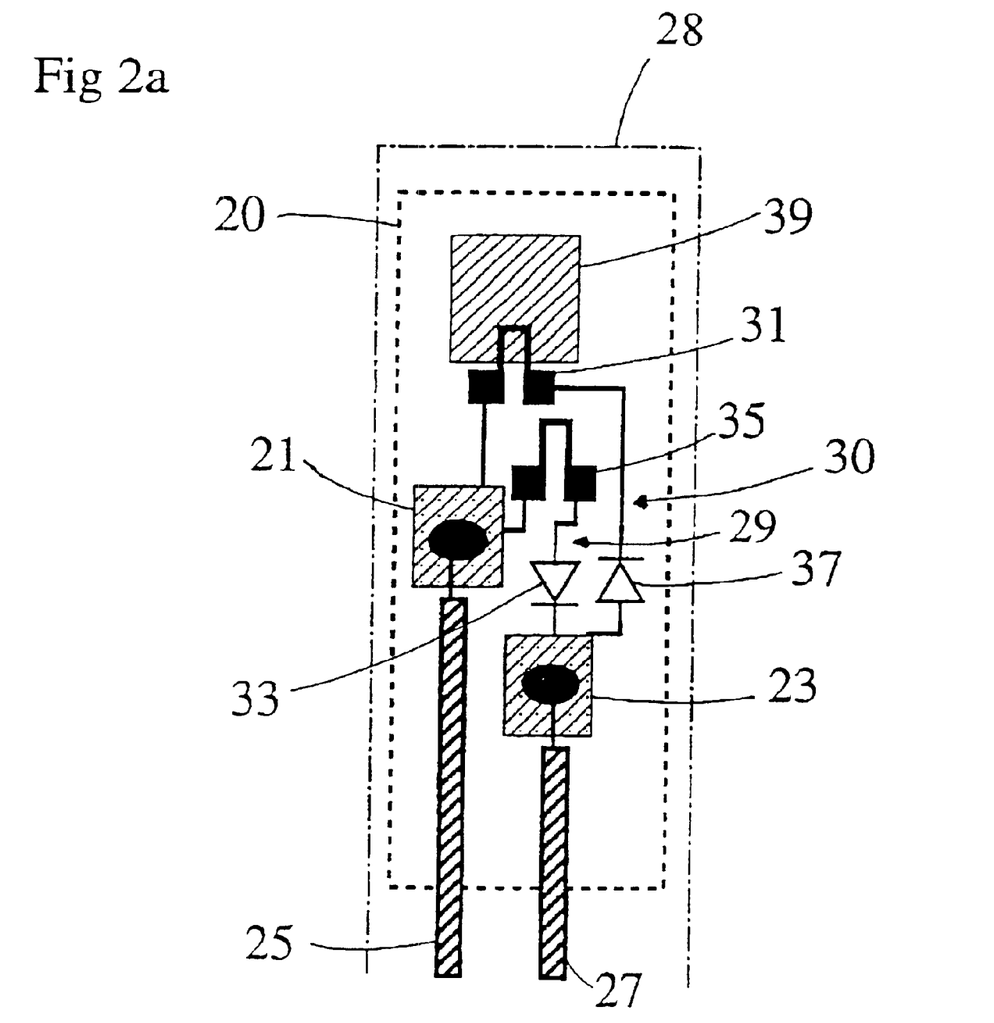
FIG. 2a shows a schematic view of a chip according to a first embodiment of the invention.

FIG. 2a is a schematic view of a chip 20 according to a first embodiment of the invention. Only two conductors 25 and 27 are connected to the chip 20 through a catheter 28. The chip 20 is adapted to be placed in one end of the catheter 28. This end of the catheter 28 could for example be inserted in a human body. The other end is kept outside the body and is connected to other components in a circuitry for processing the sensed pressure.

Figure 2B:
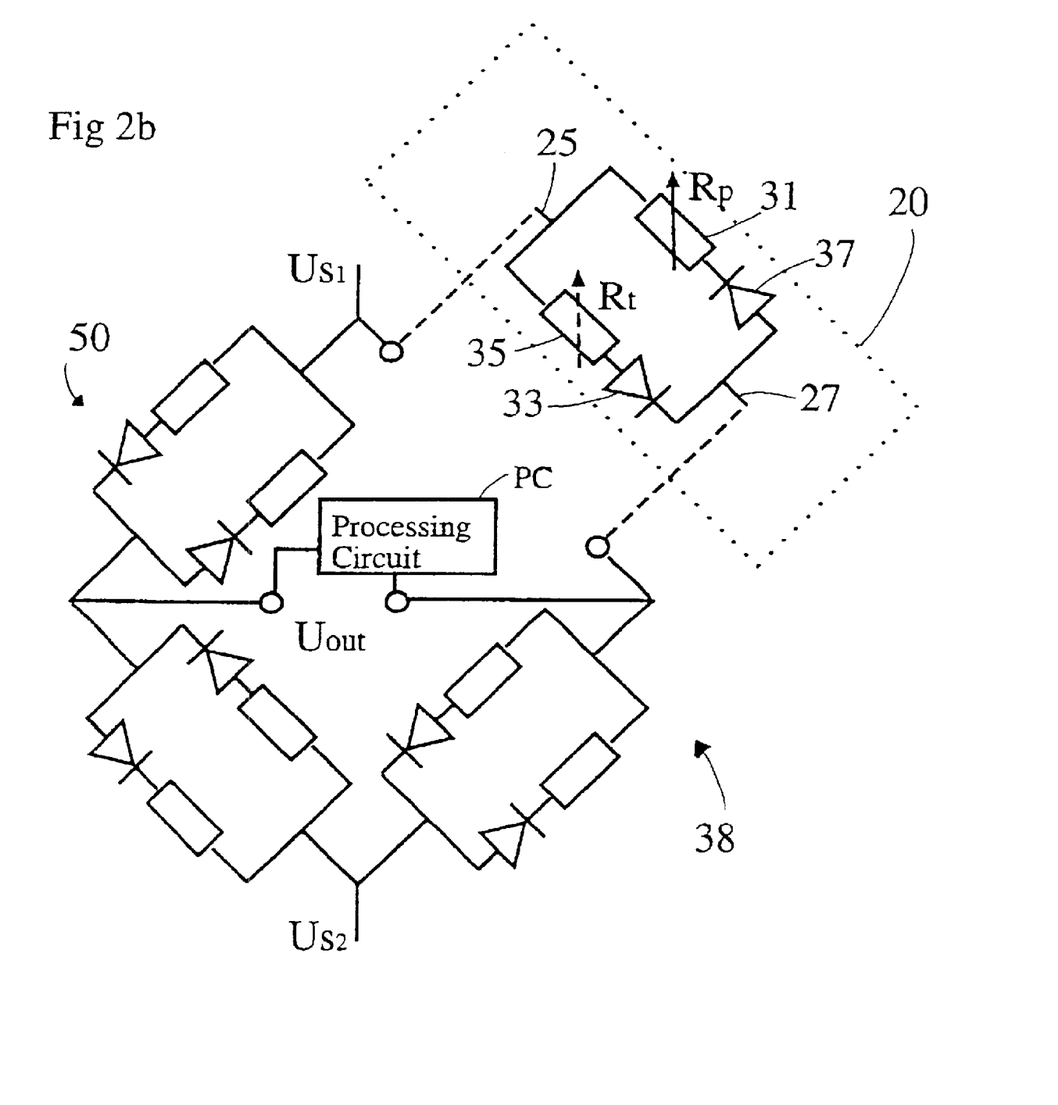
FIG. 2b shows a wiring diagram comprising the components on the chip in FIG. 2a and components outside the chip.

The chip 20 comprises a first terminal pad 21 and a second terminal pad 23. The first conductor 25 is soldered to the first pad 21 and the second conductor 27 is soldered to the second pad 23. The conductors 25,27 are isolated from each other and enclosed in the catheter 28 leading from the chip 20. The pads 21,23 are connected to each other on the chip 20 through two separate parallel branches 29,30. The first branch 29 connects the pads 21,23 through a temperature sensing element, Rt, 35 connected in series with a first diode 33. The second branch 30 connects the pads 21,23 through a pressure sensing element, Rp, 31 connected in series with a second diode 37 oriented in the opposite direction to the first diode 33. This means that the pressure sensing element 31 and the temperature sensing element 35 are connected in parallel, as apparent from FIG. 2b. FIG. 2b shows the chip 20 and the conductors 25,27 connected to a measuring circuit 38 outside the body.

Returning to FIG. 2a, the pressure sensing element 31 is in this embodiment a piezoresistor 31 that is mounted on a pressure sensitive diaphragm 39. This arrangement makes the resistance of the piezoresistor 31 depend on the pressure. A person skilled in the art is familiar with such a strain gage so the pressure sensing element 31 will not be further described herein. Piezoresistors are also temperature sensitive so the resistance will also change with temperature. However, the pressure sensing element will be referred to here as just the pressure sensing element 31. To be able to compensate for the temperature influence on the resistance in the pressure sensing element 31 a temperature sensing element 35 is provided. This element 35 is preferably a piezoresistor 35 of the same kind as the pressure sensing element 31. This resistor 35 is however not placed on a pressure sensitive diaphragm, and the resistance of this resistor 35 will only change with temperature.

Thanks to this arrangement the pressure can be measured with a good accuracy. The temperature dependence on the pressure sensing element 31 is compensated for by the temperature sensing element 35. The diodes 33,37 that are connected in opposite directions in the two branches 29,30 act as control means and enables measuring of only one of the resistances 31,35 at the time by changing the input voltage, Us, to the circuit. Not to forget is that the diodes 33,37 each has a resistance too. Their resistances are as well as the resistances of the piezoresistors dependent on the temperature. The influence from the diodes must be considered when the pressure is calculated. Since the pressure and temperature sensing elements are connected in parallel only two conductors 25,27 out from the chip 20 through the catheter 28 are necessary.

The wiring diagram in FIG. 2b comprises the components on the chip 20 in FIG. 2a and components 50 outside the chip 20 in the other end of the catheter 28. The pressure sensitive element 31 and the temperature sensitive element 35 are connected in parallel and each in series with one diode 33,37. The two diodes 33,37 are oppositely directed. The components on the chip 20 could compose one branch of a Wheatstone bridge, as apparent in the embodiment shown in FIG. 2b. The other three branches in the bridge are preferably composed in the same way and of the same components as the chip branch so as to balance the bridge and avoid offset.

Thanks to the opposite directions of the two diodes 33,37 a change in the input voltage, Us, to the bridge can alter which one of the two parallel branches 29,30 on the chip that should be included in the circuit and thus affect the output voltage, Uout, from the bridge. Thus the pressure is measured when the input voltage, Us, has its polarity in one direction and the compensating temperature is measured when the input voltage, Us, has its polarity in the opposite direction. The output voltage, Uout, is connected to a processing circuit, PC, processing the output voltages, provided from the two polarities, to derive the temperature compensated pressure.

It is possible to instead for the supply voltage, Us, use another power supply, such as a current supply. Then the current through the bridge is measured instead of the voltage drop over the bridge.

The processing circuit, PC, is necessary in this invention, as distinguished from the prior art pressure sensing devices for pressure measurements inside the body. However, this processing circuit, PC, does not have to be very expensive and since it is provided outside the body it can be used for many measurements unlike the chip that most often is used only for one measurement.

The processing is made by simple calculations apparent for the person skilled in the art and is therefore not described in detail. Even though the processing circuit, PC, is needed, its particular processing features are not a part of the actual invention. The processing could for example be performed by first measuring one of the two sensing elements, i.e. the pressure sensitive piezoresistor or the temperature sensitive piezoresistor in this embodiment, and store this value temporarily. Then the other sensing element is measured and the two measurements are compared and used for the calculation of the actual pressure. Values from a calibration of the chip elements are also used for this calculation. From this calibration the relation between the pressure sensitivity and temperature sensitivity, for the two sensitive elements is known.

Figure 3A:
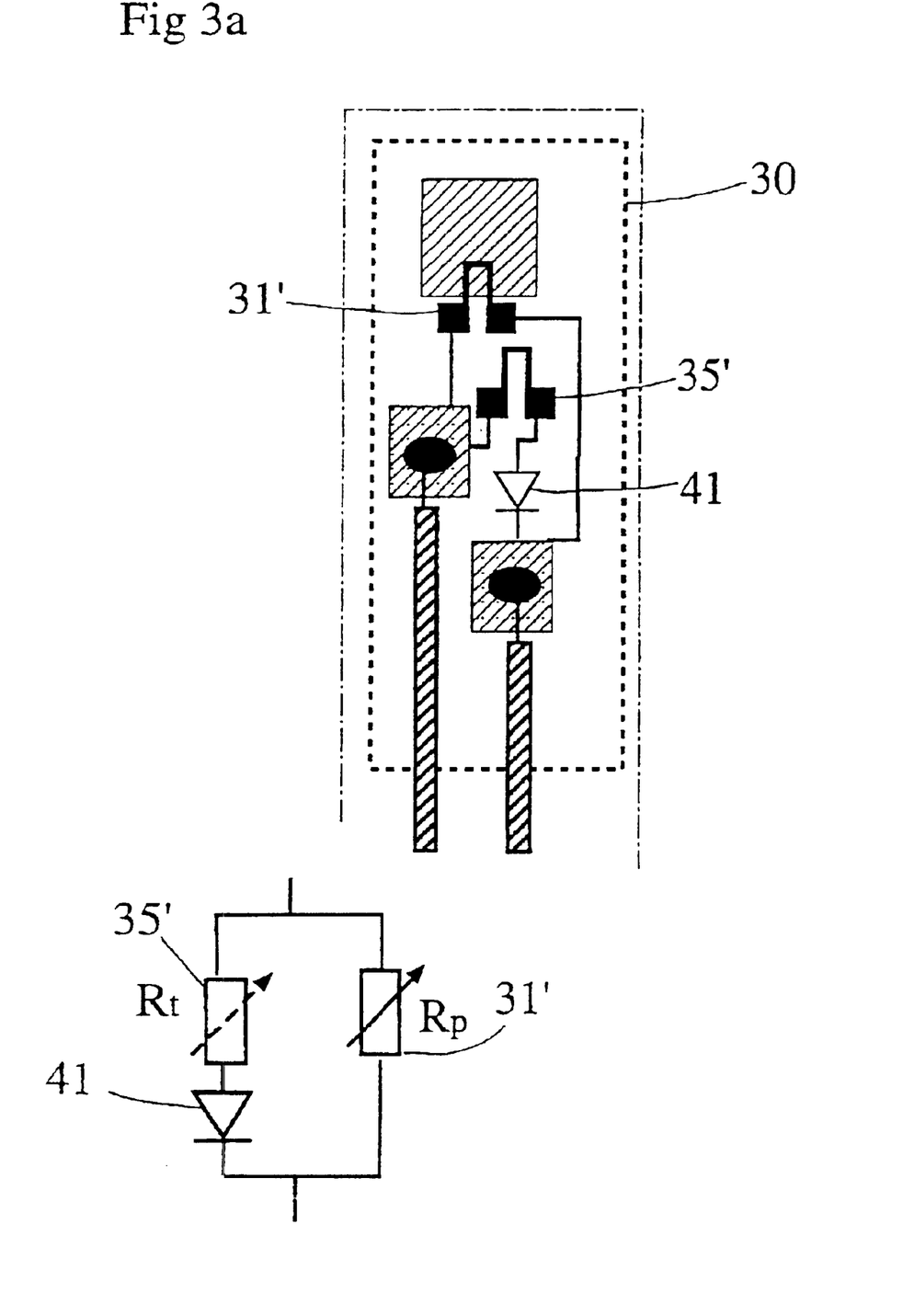
FIG. 3a shows a schematic view of the chip design and the chip part of a wiring diagram according to a second embodiment of the invention.

FIG. 3a shows a schematic view of a chip 30 and the chip part of a wiring diagram according to a second embodiment of the invention. In this embodiment only one control means 41 is needed. The control means 41 is in this embodiment a diode 41. It is connected in series with the temperature measuring element 35'. This implies that either is the output voltage from the bridge dependent on both the piezoresistors 31', 35' and the diode 41 or just the piezoresistor 31' which is dependent on the pressure. The needed compensation factor for the temperature dependence could however be calculated from these two measurements having the input voltage polarised in two opposite directions. The influence on the measured resistance from the diode 41 has to be considered since the resistance of the diode 41 also is temperature dependent. The processing circuit, PC described in the first embodiment is of course used even in this embodiment and can be used in all the further described embodiments for calculating the pressure from the measured values. As in the first embodiment the branches (not shown) of the bridge outside the chip should preferably be configured like the one on the chip so as to balance the bridge and avoid offset. It is also possible to connect the only diode in series with the pressure sensing element instead of in series with the temperature sensing element.

Figure 3B:
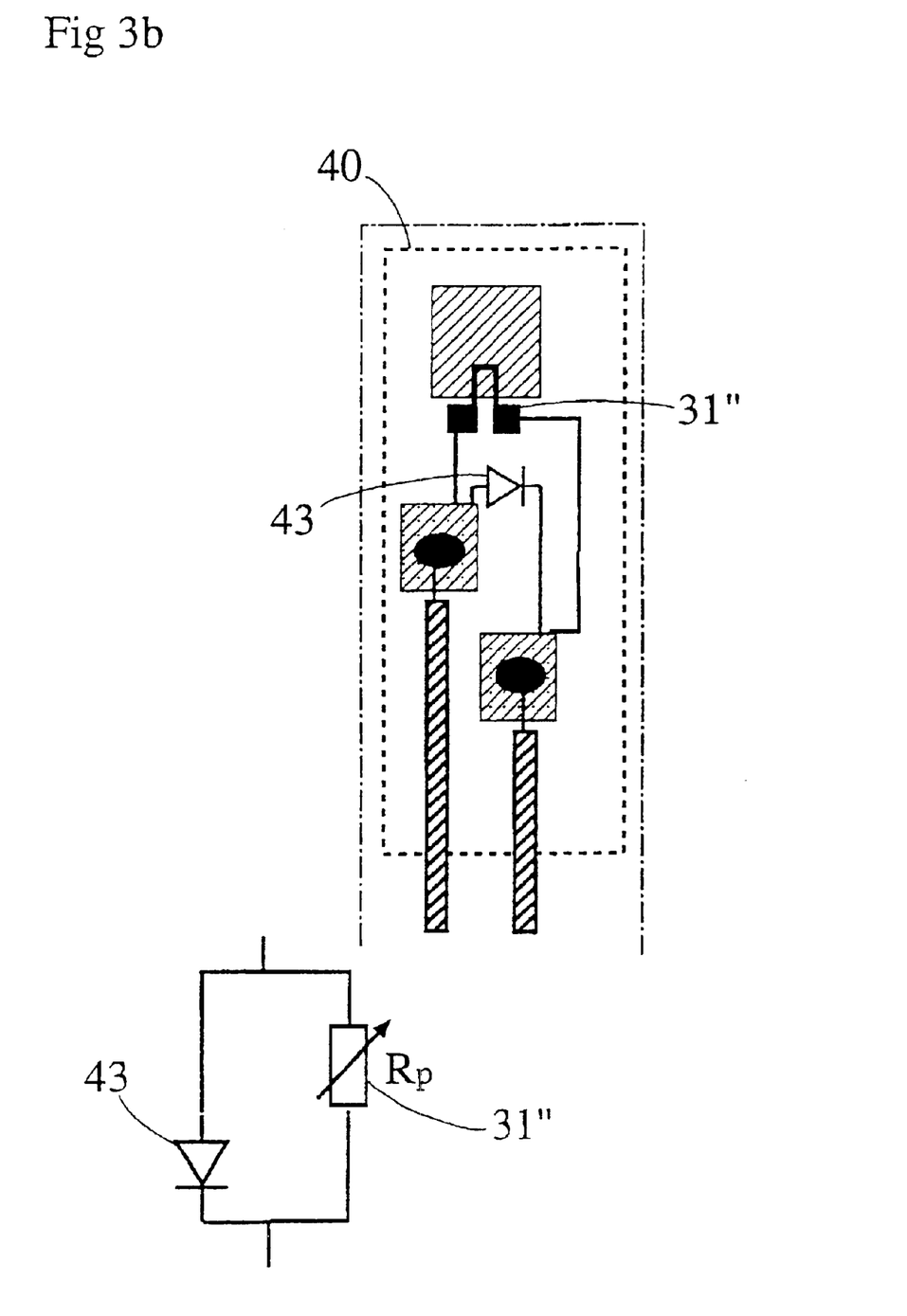
FIG. 3b shows a schematic view of the chip design and the chip part of a wiring diagram according to a third embodiment of the invention.

FIG. 3b shows a schematic view of a chip 40 and the chip part of a wiring diagram according to a third embodiment of the invention. In this embodiment a diode 43 is used as a temperature sensing element for measuring the temperature and as control means. This implies that the temperature sensitive piezoresistor 35, 35' used in the first and second embodiments is not needed. As in the second embodiment the output voltage from the bridge is either dependent on both the pressure sensitive resistor 31" and the diode 43 or just the pressure sensitive resistor 31". The input voltage decides which one of the mentioned alternatives that is chosen. The diode and the resistor in FIG. 3b could also be coupled in series. In this case the amplitude of the voltage/current source is used to separate the different measurements. In the third embodiment the branches (not shown) of the bridge outside the chip each should be provided with a diode in parallel with the resistor to balance the bridge and to avoid offset.

Figure 3C:
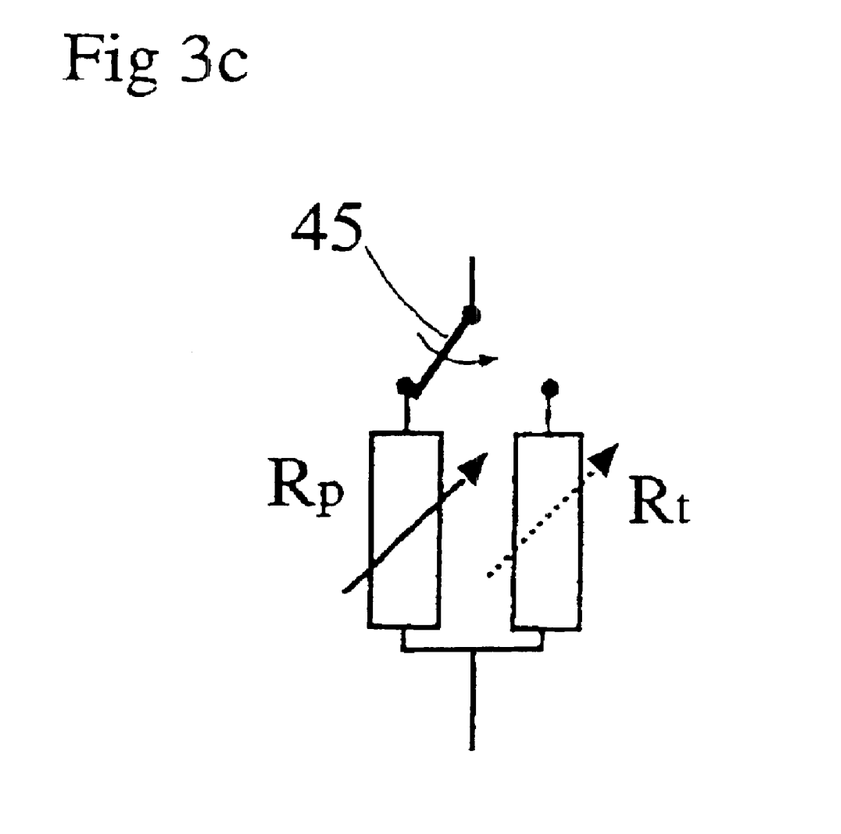
FIG. 3c shows the chip part of a wiring diagram according to a fourth embodiment of the invention.

FIG. 3c shows the chip part of a wiring diagram according to a fourth embodiment of the invention. In this embodiment a mechanical switch 45 is used as control means instead of diodes to switch between pressure and temperature measurements. In this embodiment only two branches are shown but it is if needed possible to switch between more than two branches. The branches of the bridge outside the chip comprise only one resistor each of the same type as the resistors on the chip. The switch 45 could be of a kind making a switch from one coupling direction to the other in dependence of the direction of the input voltage to the bridge circuitry and it is manufactured on the chip with micro machining fabrication techniques. The switch 45 could also be of a kind making a switch in dependence of the frequency of an AC supply. Then, the bridge is designed to be operated with and to process at least two kinds of AC supply frequencies.

In the above described embodiments the pressure and the temperature has been measured, but the idea of the invention is applicable even for other measurements where an external stimulus changes the resistance or the capacitance in proportion to the stimulus. For example the flow rate could be measured by means of a flow rate sensing element. This flow rate sensing element is a mechanical sensing element just like the pressure sensing element in that sense that they both respond with actual mechanical movements to a change in pressure or flow rate.

Figure 3D:
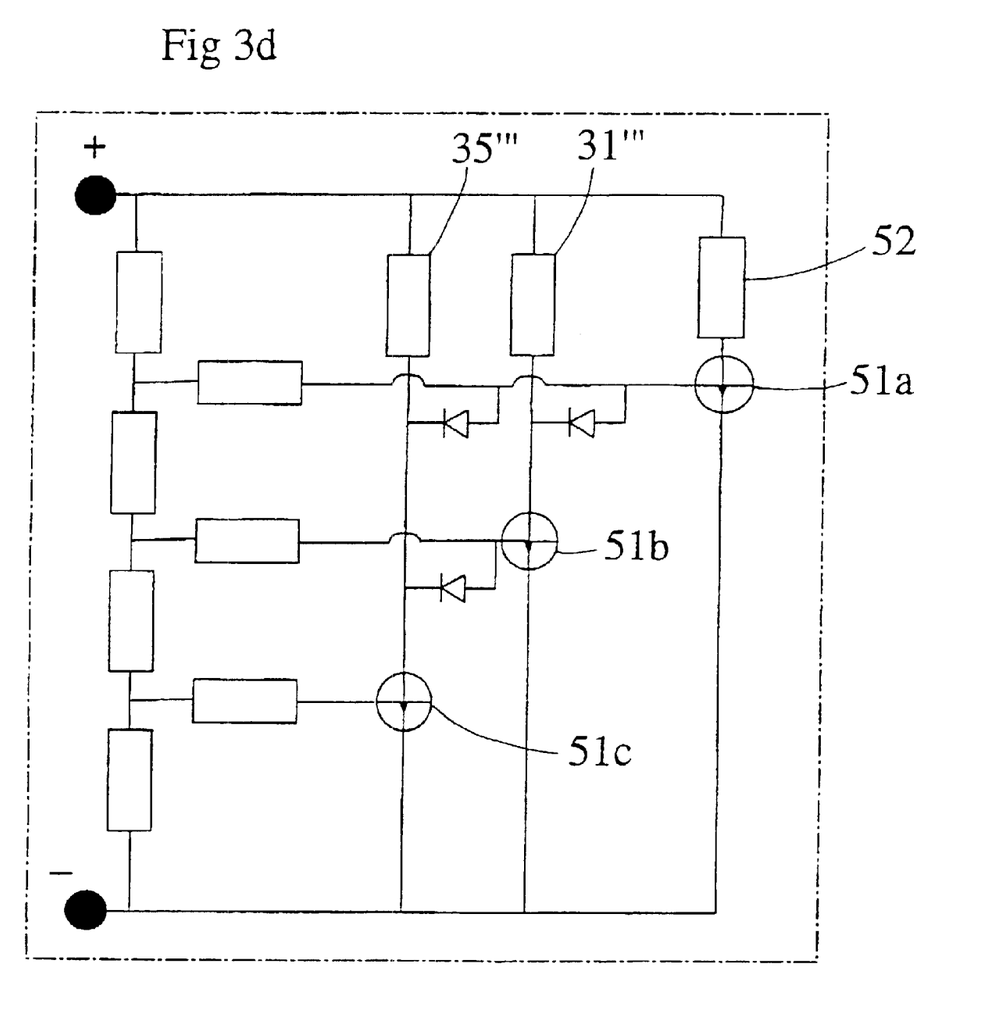
FIG. 3d shows the chip part of a wiring diagram according to a fifth embodiment of the invention.

FIG. 3d shows the chip part of a wiring diagram according to a fifth embodiment of the invention. Here transistors 51a,51b,51c are used as control means for switching between pressure measurements, temperature measurements and flow rate measurements. The flow rate is measured by a flow rate sensing element 52. The pressure and the temperature is measured as before by a pressure sensing element 31''' and a temperature sensing element 35'''. Transistors are preferably used for the switching between different parallel branches if there are more than two branches. In this embodiment three parallel branches are shown. The seven resistors in the figure that lack references are provided for producing the needed voltage division to open and close the different transistors. The wiring diagram is easily understood for a person skilled in the art and will not be further described inhere. The wiring diagram could also be varied in a number of ways to give a voltage division needed for opening or closing the transistors. The supply voltage controls the transistors and thereby chooses to measure one of the branches or maybe more than one of the branches at the same time.

If more than one feature should be measured, for example both pressure and flow rate, it could be advantageous to measure the temperature individually for each feature. Then two temperature sensing elements are needed. They could be connected one in parallel with the pressure sensing element and one in parallel with the flow rate sensing element. Each component could also be connected in series with a diode or a transistor. The two branches with each two parallel connected elements could be connected in parallel with for example a mechanical switch in between. The same idea could of course be used even with more elements and more branches.

Figure 4:
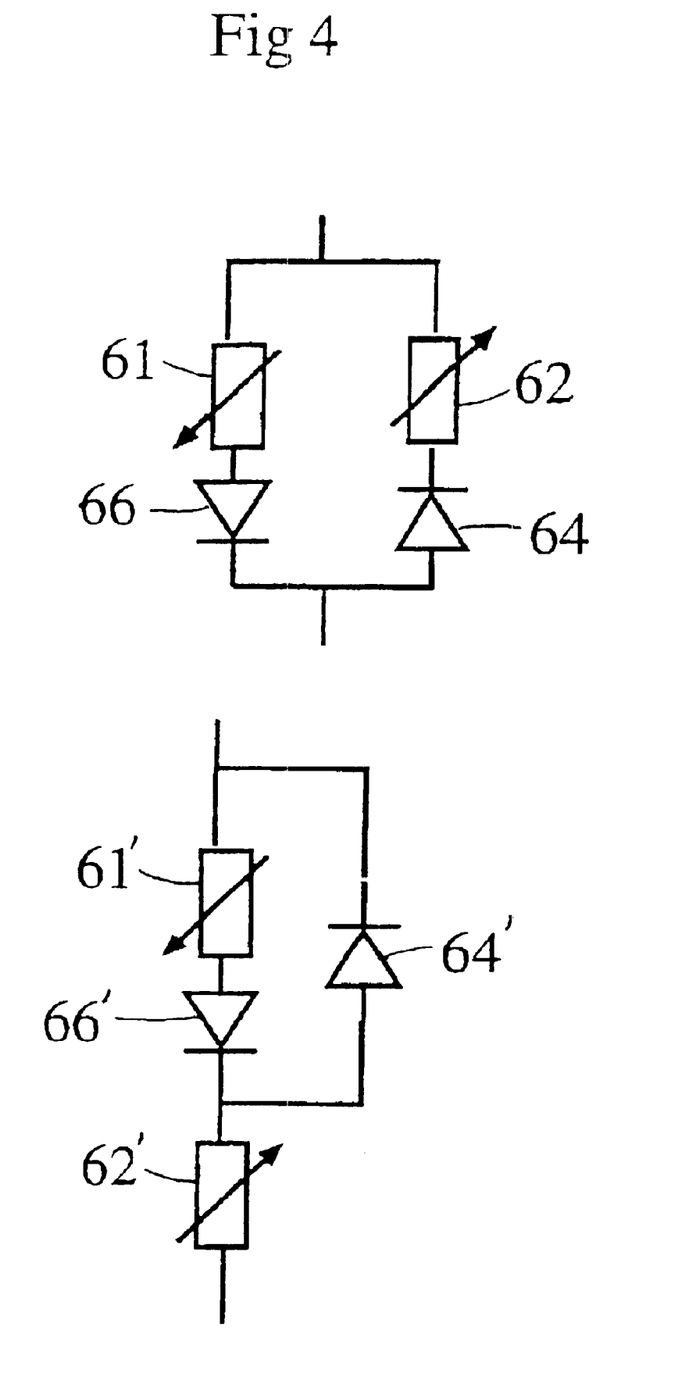
FIG. 4 shows the chip part of a wiring diagram according to a sixth embodiment of the invention in two slightly different variants.

FIG. 4 shows the chip part of a wiring diagram according to a sixth embodiment of the invention. In this embodiment two piezoresistors 61,62 of the same type are used. They are both pressure sensitive and temperature sensitive. But they could also both be flow rate sensitive and temperature sensitive. In this embodiment an increased pressure will decrease the resistance in one of the resistors 61 and increase the resistance in the other 62. One method to achieve this is to place one of the resistors 61 on one side of the above mentioned pressure sensitive diaphragm and the other resistor 62 on the other side. One of the resistors 61 will thus experience an inward bent from the diaphragm and the other 62 an outward bent. However, the resistors does not need to respond to a pressure change with opposite signs. The temperature will increase the resistance in both resistors 61,62, but not necessary by the same amount. The resistors 61,62 are connected in series with one diode 64,66 each and in parallel with each other. Like in the above described embodiments the resistors 61,62 could be measured one at the time by changing the input voltage from the power supply outside the chip. The processing circuit can then, by means of the two measurements and of course calibration values from all the components, calculate the actual temperature and thus also the actual pressure.

An alternate way of connecting the resistors of the sixth embodiment is also shown in FIG. 4. Here two diodes 64', 66' are provided to the circuit such that either one resistor 62' is measured together with a diode 64' or two resistors 62', 61' are measured in series together with one diode 66' in dependence of the input power. As in all the above described embodiments the processing circuit is used to calculate the wanted values.

Figure 5A:
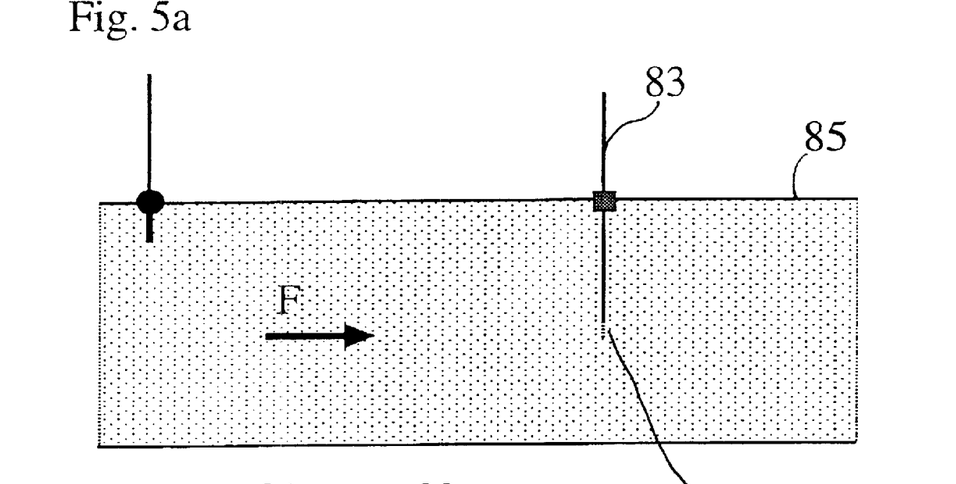
FIGS. 5a–c show a schematic view of a chip and the chip mounted on a catheter and also inserted into a tube filled with a conductive liquid according to a seventh embodiment of the invention.
Figure 5B:
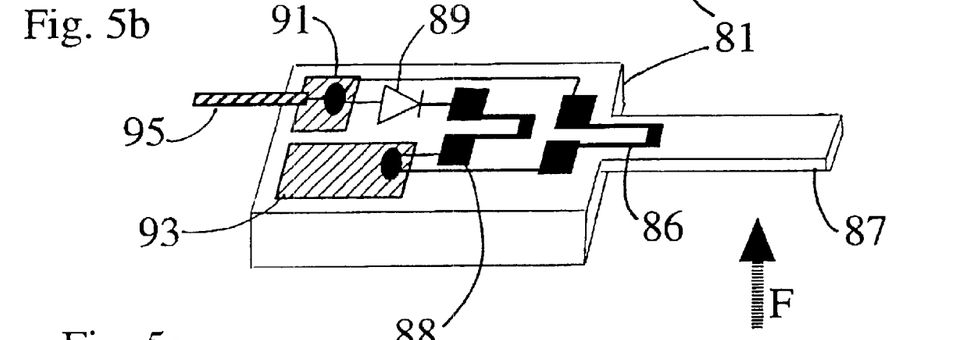
Figure 5C:
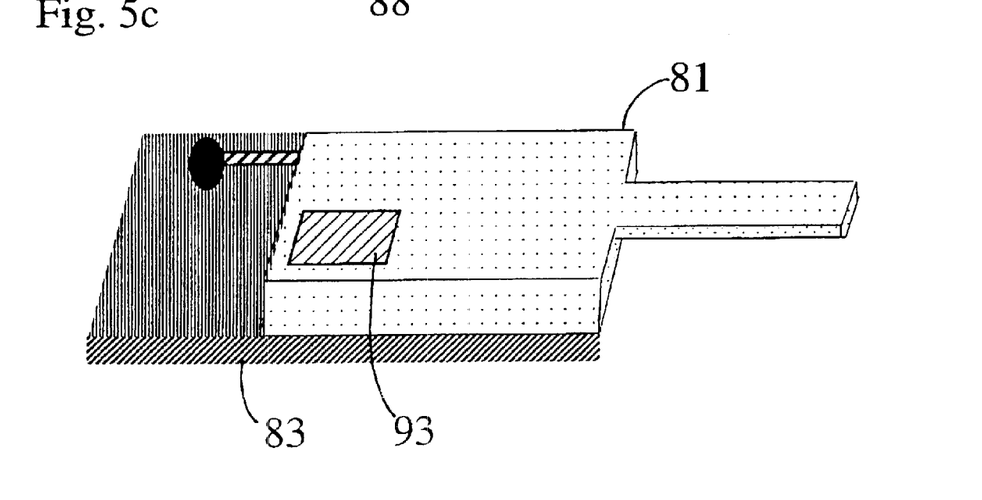

FIG. 5a-c show a seventh embodiment of the invention, where a chip 81 is mounted on a catheter 83 and inserted into a tube 85 for measuring the flow rate in the tube 85. FIG. 5a shows the tube 85 in cross section. The tube 85 contains a conductive liquid flowing in the tube with a flow rate F. The catheter 83 is inserted into the tube and the chip 81, shown as a dashed line, is mounted at the end of the catheter. The tube 85 is connected to one side of the measuring unit. FIG. 5b is a schematic view of the chip 81. The chip 81 comprises a flow rate sensing element 86. It is a resistor partly placed on a projecting part 87 of the chip 81. This projecting part 87 is bent in proportion to the flow rate in the liquid and thus also the resistance of the flow rate sensing element 86 changes in proportion to the flow rate. The flow rate sensing element 86 is connected in parallel with a diode 89 and a temperature sensing element 88 provided to compensate for the temperature dependence in the flow rate sensing element. One end of the parallel connected components is connected to a first pad 91 and the other end is connected to a second pad 93 in the same way as described more clearly in the first embodiment. The first pad 91 is connected to the catheter 83 through an isolated conductor 95. FIG. 5c shows the chip 81 in FIG. 5b mounted on the catheter 83. The entire chip 81, except from the second pad 93, is covered by some isolating material. The catheter is also isolated. In this embodiment the catheter 83 itself is used as one of the conductors out from the chip 81 and the conductive liquid in the tube is used as the other conductor.

Figure 6:
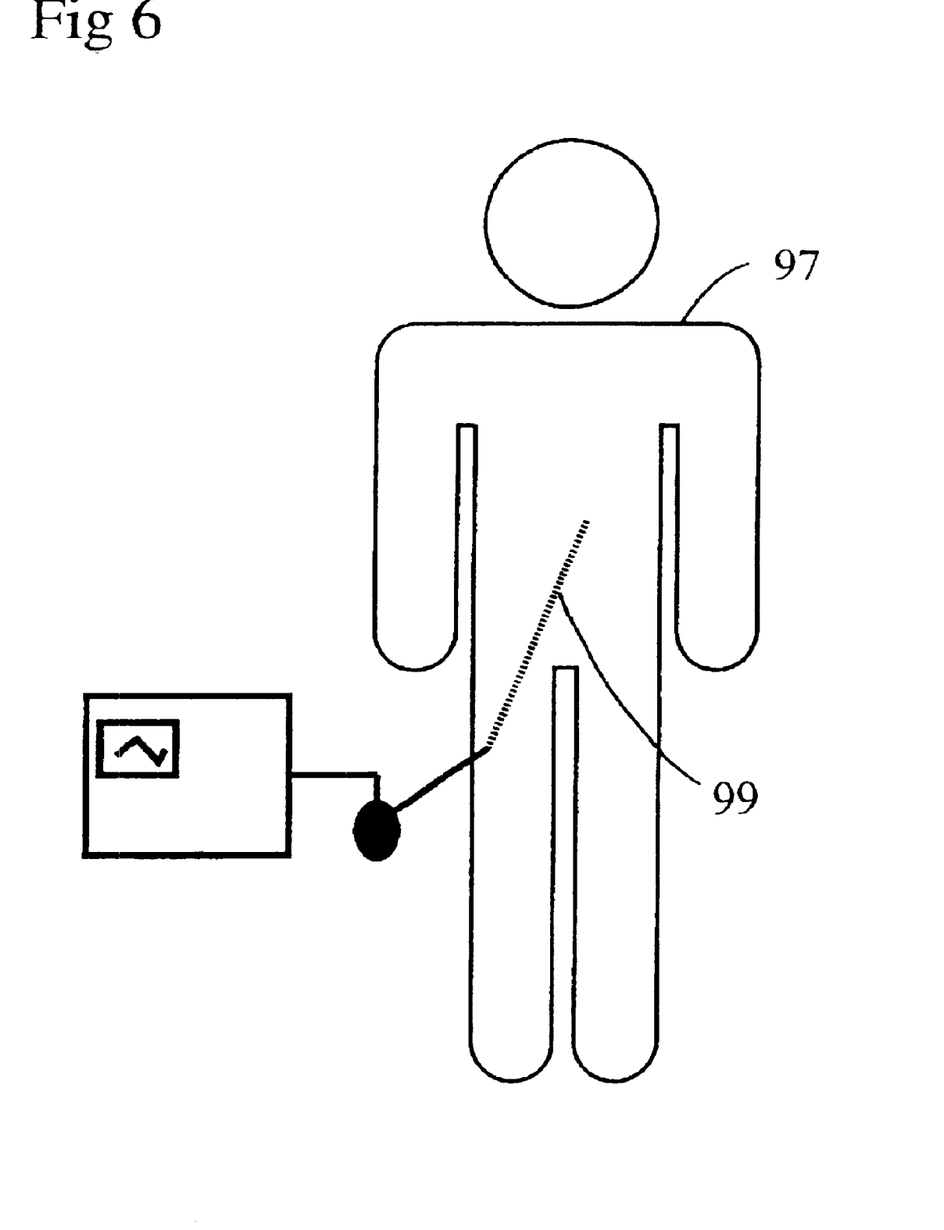
FIG. 6 is a schematic view of an eighth embodiment of the invention.

FIG. 6 is a schematic view of an eighth embodiment of the invention. It shows a human body 97 with a catheter 99 inserted for measuring for example the flow rate or the pressure in for example the blood. A chip according to any one of the previous described embodiments is mounted in the end of the catheter 99. In this embodiment the catheter 99 with the sensing elements that could sense at least two phenomena using at the most two conductors have been isolated and prepared for use inside a human body 97.

Figure 7:
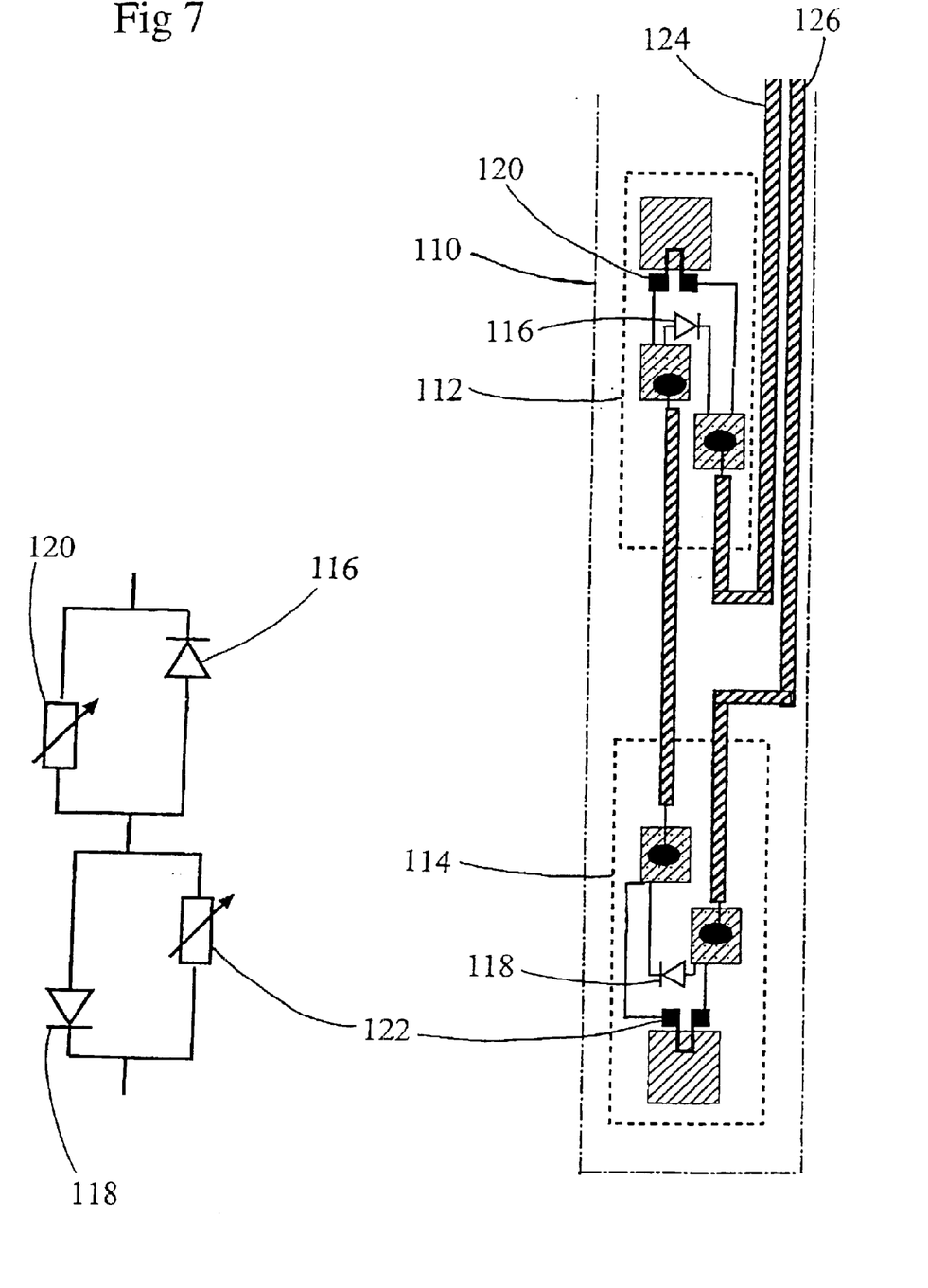
FIG. 7 is a schematic view of a coupling with two sensing devices according to a ninth embodiment of the invention.

FIG. 7 shows a schematic view of the end of a catheter 110 on which two chips 112, 114 are mounted according to a ninth embodiment of the invention. A wiring diagram according to this embodiment is also shown. In this embodiment two sensing devices configured as in the third embodiment are mounted and/or fabricated on the same catheter 110 but on two different chips 112, 114. The two sensing devices are coupled in series. It would also be possible to connect them in parallel. Each sensing device comprises as in the third embodiment a diode 116, 118 working as both temperature sensing element and control means and a pressure sensitive resistor 120, 122. The two diodes 116, 118 are connected in opposite directions. By measuring the temperature sensitive forward offset of the diode the temperature can be determined and used to compensate for temperature dependencies of the sensing elements. This measurement is typically performed by alternating the voltage and measuring the current. The pressure sensitive resistor could be measured and temperature compensated in the same way as described for the previous embodiments with fixed amplitude. The different chips are addressed by changing the polarity. Thus, by using the possibility to change both the polarity/phase and the amplitude of the voltage/current supply and by using the diodes as both temperature sensing elements and control means two different temperatures (one of each chip) as well as two different pressures (one of each chip) could be measured using at the most two conductors 124, 126 out from the catheter 110.

The embodiments discussed above could be changed in a number of ways. For example the diodes could be replaced by a series of diodes or diodes in parallel. This would increase the balance and thus decrease manufacturing differences. It is also possible instead of changing the voltage or the current in purpose to measure the different features to use an AC circuitry and to alternate the frequency. The control means are then arranged to be controlled by frequency changes of the input voltage.

The diodes shown in the different embodiments above could be replaced by elements, for example transistors, turned on and turned off, respectively, by different voltages.

The branches of the bridge outside the chip could also be built up in a different way. It is even possible to do the measurements without a bridge circuit.

In these embodiments the pressure and flow rate sensing elements have been piezoresistors, but there are other possibilities to measure pressure and flow rate. One example is to use a capacitor that changes its capacitance due to pressure or flow rate changes.

Other possible quantities to measure instead of pressure and flow are oxidine, potassium, chlorine levels in liquids or impedance and capacitance measurements.

It should be noted that each time this text refers to a catheter a guide wire could be used instead.

What is claimed is:

1. Sensing device for measuring at least two features, wherein said features include pressure and temperature, flow rate and temperature or pressure, and flow and temperature, in a fluid, comprising at least two sensing elements all mounted and/or fabricated on a chip and connected to a chip circuit, and a power supply and measuring circuit placed outside the chip and connected to the chip circuit, wherein the power supply and measuring circuit is controllable to feed at least two different kinds of signaling to the chip circuit; and in that the at least two sensing elements are connected to each other and to the power supply and measuring circuit such that at least one of the sensing elements in dependence of the different signaling from the power supply could be individually measured, and in that the chip is adapted to be mounted on a catheter or a guide wire.

2. Sensing device according to claim 1, wherein at least one of the sensing elements is a temperature sensing element provided to compensate for the temperature dependence in the other sensing elements; in that all the sensing elements are connected in parallel with one another; and in that at least one of the parallel coupled elements is connected in series with control means permitting current to pass only when it is controlled in such sense from the power supply and measuring circuit.

3. Sensing device according to claim 2, wherein a first conductor is connected to one side of the parallel connected sensing elements and a second conductor is connected to the other aide of the parallel connected sensing elements, whereby the conductors either both are enclosed in a catheter leading from the chip or one of the conductors is the catheter itself and/or one of the conductors is a conductive liquid or gas or a combination of them in where the feature is measured.

4. Sensing device according to claim 1, wherein at least one of the sensing elements is a temperature sensing element provided to compensate for the temperature dependence in the other sensing elements; in that each of the other sensing elements is connected in parallel with one individual of the at least one temperature sensing element; and in that at least one of the parallel coupled elements in each parallel connection is connected in series with control mean permitting current to pass only when it is controlled in such sense from the power supply and measuring circuit.

5. Sensing device according to claim 4, wherein the at least one control means only permits rectified current in one direction to pass and in that the control of the power supply is provided by polarising its supply voltage or current in opposite directions.

6. Sensing device according to claim 5, wherein the control means is at least one diode.

7. Sensing device according to claim 1, herein at least one of the sensing elements is a mechanical sensing element that responds to a change in the measured feature with an actual mechanical movement.

8. Sensing device according to claim 1, herein the catheter or guide wire is adapted to be inserted into a body for in vivo measurements.

9. Sensing device according to claim 1, wherein the connected sensing elements on the chip together form one branch of a Wheatstone bridge where the power supply and the measuring circuit outside the chip comprises the other branches of the bridge.

10. Sensing device according to claim 1, wherein it comprises processing means, PC, connected to a measuring output of the measuring circuit, the processing means being adapted to store the output after each control from the power supply and by comparing the stored values with calibration values for the sensing elements concerned provide as an output value the temperature compensated sensed feature.

11. Sensing device according to claim 1, wherein the sensing device is adapted to measure at least two different phenomena and transmit at least two different measurements through at the most two conductors.

12. Sensing device according to claim 1, wherein the sensing elements comprise at least one temperature sensing element and at least one temperature and pressure sensing element, the temperature sensing element being a piezoresistor and/or a diode and the temperature and pressure sensing element being a piezoresistor lying on a pressure sensitive diaphragm.

13. A sensing device according to claim 1 wherein the sensing device is adapted to be coupled in series or in parallel to at least one other sensing device such that the two sensing devices are separated and different measurement values can be achieved from the two separated sensing devices.

14. A method for measuring at least two different features in a fluid, wherein said features include pressure and temperature, flow rate and temperature or pressure, and flow and temperature, wherein the measuring being provided by at least two sensing elements all mounted and/or fabricated on a chip and connected to a chip circuit, the chip circuit being connected to a power supply and a measuring circuit placed outside the chip, wherein mounting the chip on a catheter or a guide wire and inserting the catheter or guide wire into the actual measuring place and controlling the power supply and measuring circuit to feed at least two different kinds of signals to the chip circuit, measuring at least two different features and deriving a value in a processing means connected to a measuring output of the measuring circuit by comparing the at least two different measurements, the derived value being the temperature compensated value for at least one of the features.

15. A method according to claim 14, wherein controlling the power supply by changing the direction and/or the output level of a DC supply and/or by changing the frequency and/or amplitude of an AC supply.

16. A method according to claim 14, wherein connecting at the most two conductors to the chip.

17. A method according to any one of the claims 14, wherein using the catheter or guide wire as one of the conductors.

18. A method according to claim 14, wherein at least two separate sensing devices are mounted on a catheter and connected in series or in parallel, and wherein the sensing devices are connected to two outgoing conductors such that different measurement values can be derived from each sensing device by changing the polarity/phase and/or the amplitude of the voltage/current supply.

* * * * *